United States Patent [19]

Catalani

[11] Patent Number: 5,146,916
[45] Date of Patent: Sep. 15, 1992

[54] ENDOTRACHEAL TUBE INCORPORATING A DRUG-IRRIGATION DEVICE

[76] Inventor: Angelo S. Catalani, Via dei Colli 7, 00198 Roma, Italy

[21] Appl. No.: 637,078

[22] Filed: Jan. 3, 1991

[30] Foreign Application Priority Data

| Jan. 5, 1990 | [IT] | Italy | 47503 A/90 |
| Jan. 25, 1990 | [IT] | Italy | 47566 A/90 |
| Feb. 5, 1990 | [IT] | Italy | 47601 A/90 |
| Feb. 14, 1990 | [IT] | Italy | 47628 A/90 |
| Dec. 12, 1990 | [IT] | Italy | 48560 A/90 |

[51] Int. Cl.⁵ .................... A61M 16/04; A61M 25/10
[52] U.S. Cl. ......................... 128/207.14; 128/207.15; 128/750; 128/911; 128/912; 604/43; 604/257; 604/264; 604/280
[58] Field of Search ....... 128/207.14, 207.15, 128/203.12, 911, 912, 750; 604/43, 257, 261, 264, 280, 128, 40

[56] References Cited

U.S. PATENT DOCUMENTS

| 3,114,373 | 6/1962 | Andersen | 128/207.15 |
| 3,173,418 | 3/1965 | Baran | 128/207.15 |
| 3,638,655 | 2/1972 | Doherty | 128/207.15 |
| 3,788,326 | 1/1974 | Jacobs | 128/207.15 |
| 3,981,299 | 9/1976 | Murray | 604/43 |
| 4,214,593 | 7/1980 | Imbruce et al. | 128/748 |
| 4,327,720 | 5/1982 | Brunson et al. | 128/911 |
| 4,364,394 | 12/1982 | Wickinson | 604/96 |
| 4,417,576 | 11/1983 | Baran | 128/207.15 |
| 4,437,856 | 3/1984 | Valli | 604/29 |
| 4,453,545 | 6/1984 | Inoue | 128/911 |
| 4,501,580 | 2/1985 | Glassman | 604/43 |
| 4,584,998 | 4/1986 | McGrail | 128/207.15 |
| 4,607,635 | 8/1986 | Heyden | 128/207.15 |
| 4,674,495 | 6/1987 | Orr | 128/912 |
| 4,693,243 | 9/1987 | Buras | 128/207.15 |
| 4,739,756 | 4/1988 | Horn | 128/207.15 |
| 4,821,714 | 4/1989 | Smelser | 128/207.15 |
| 4,840,173 | 6/1989 | Porter, III | 128/911 |
| 4,955,375 | 9/1990 | Martinez | 128/207.15 |
| 4,977,894 | 12/1990 | Davies | 128/207.15 |
| 5,015,232 | 5/1991 | Maglinte | 604/96 |
| 5,029,580 | 7/1991 | Radford | 128/207.14 |

FOREIGN PATENT DOCUMENTS

| 1513495 | 6/1978 | United Kingdom. |
| 2003038 | 3/1979 | United Kingdom | 128/207.15 |

Primary Examiner—Edgar S. Burr
Assistant Examiner—Eric P. Raciti
Attorney, Agent, or Firm—Cohen, Pontani, Lieberman & Pavane

[57] ABSTRACT

An endotracheal tube is equipped for delivering a drug externally of the tube. The endotracheal tube includes a tube body having proximal end and distal ends, and at least one flexible irrigation cannula extending along the endotracheal tube body to its distal end. An irrigation diffuser means is attached to the irrigation cannula for spraying a drug delivered through the irrigation cannula externally of the endotracheal tube body. The endotracheal tube is particularly intended for artificial ventilation in surgical operations and in intensive resuscitation treatments. It is useful for the repeated administration and re-administration of drugs, for instance, of local anesthetics, anti-inflammatories and mucolytics in the course of intubation.

2 Claims, 4 Drawing Sheets

ENDOTRACHEAL TUBE INCORPORATING A DRUG-IRRIGATION DEVICE

BACKGROUND OF THE INVENTION

The present invention relates to medical-surgical devices for intubation, and in particular to endotracheal or other tubes intended to be inserted within the trachea of a patient for effecting artificial ventilation in surgical treatments requiring general anesthesia or in intensive resuscitation treatments.

In surgical treatments requiring general anesthesia and in intensive resuscitation treatments, it is frequently necessary and advisable to subject a patient to laryngotracheal anesthesia and/or anti-inflammatory and mucolytic treatments localized at the place of traumas resulting from the intubation or from the introduction of a foreign body constituting the endotracheal tube.

In accordance with a known technique, the administration of local anesthetics, anti-inflammatory and fluidizing drugs is effected by insertion of a suitable cannula into the trachea of the patient before intubation with the endotracheal tube, the cannula being then removed to permit the introduction of the tube. However, once the endotracheal tube has been inserted, the administration of drugs consisting of local anesthetics, anti-inflammatories and mucolytics cannot be repeated.

In fact, the endotracheal tubes in accordance with the prior art are differently shaped and devised as well as provided with many necessary devices such as secondary canalizations for various purposes, but none specifically intended for the effective administration of drugs such as local anesthetics, anti-inflammatories and fluidizers with constant intubation.

OBJECTS OF THE INVENTION

A main object of the present invention is therefore to provide a modified endotracheal tube that permits the repeated administration of drugs such as local anesthetics, anti-inflammatories and mucolytics, even during intubation of such tube in such manner as to attain a prompt laryngotracheal topical anesthesia or an anti-inflammatory action in said anatomic structures which is reproducible and that avoids reducing the pharmacological effectiveness covered by a previous administration.

Another object of the present invention is to achieve the above object with optimal diffusion of the administered drugs.

Still another object of the present invention is to achieve the previous objects through a device that does not impede intubation by the modified endotracheal tube, or in any way make it more complicated for the operator, or more traumatic for the patient.

A further object of the present invention is to attain the above objects by a device that, furthermore, avoids interfering with the functions of the endotracheal tube with which it is associated.

SUMMARY OF THE INVENTION

The foregoing and other objects are obtained through an endotracheal tube particularly intended for artificial ventilation in surgical operations and intensive resuscitation treatments in accordance with the present invention. The inventive tubes comprise independent secondary canalization for the repeated administration and passage of drugs—particularly local anesthetics, anti-inflammatories and mucolytics—during the course of intubation. In this connection, the inventive tube is provided with a distal end that is associated externally with the endotracheal tube and is suitable for spraying said drugs through a plurality of micrometric openings. Such distal end can debouch into similarly perforated chambers developed on the outside around the distal segment of said endotracheal tube.

BRIEF DESCRIPTION OF THE DRAWINGS

Further characteristics and advantages of the device in accordance with the present invention will become apparent from the following detailed description of certain of its embodiments which are preferred but not exclusive, and given by way of illustration and not of limitation, in the accompanying drawings, in which.

DETAILED DESCRIPTION OF THE PREFERRED EMBODIMENTS

Figure 1:
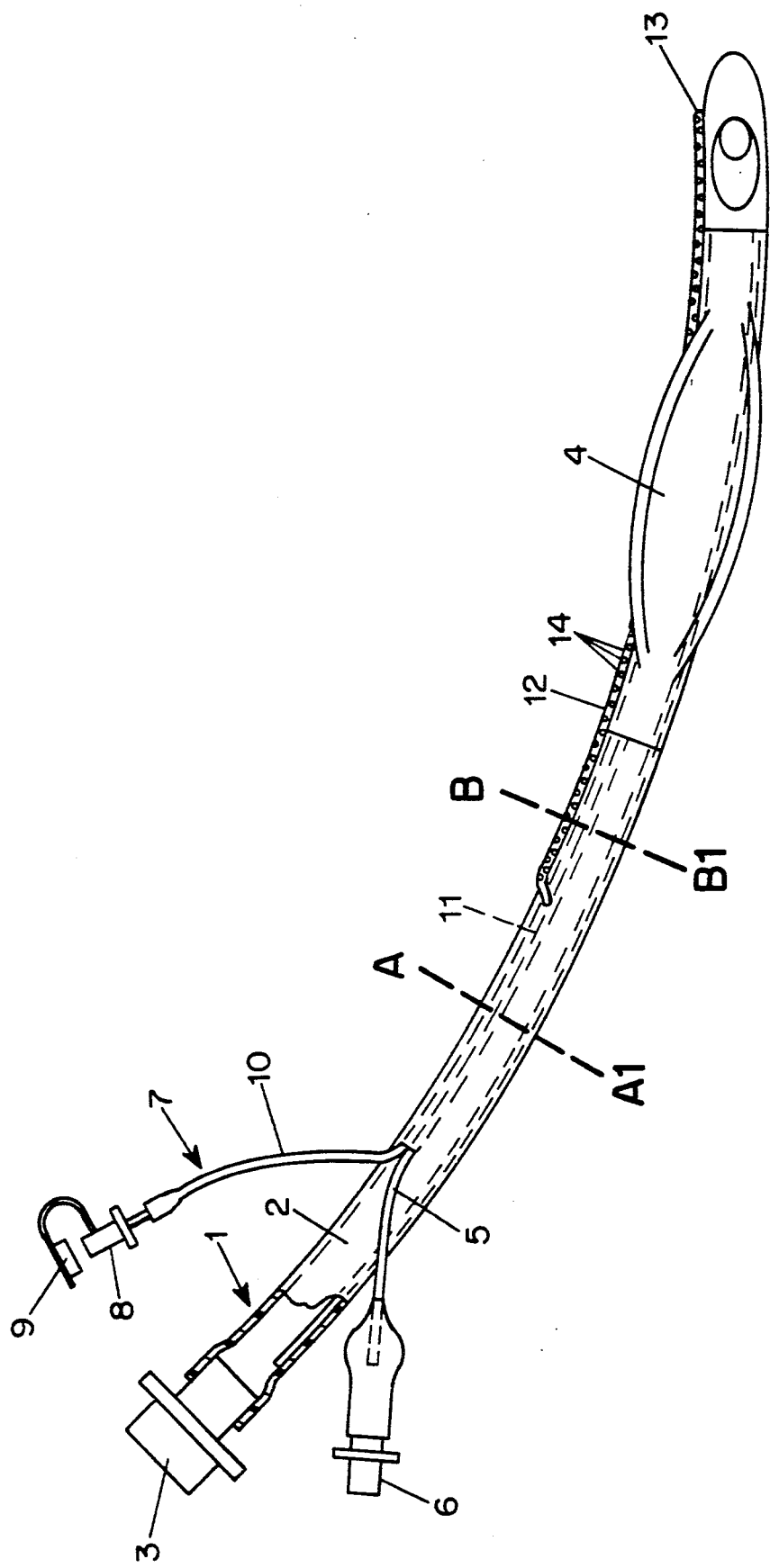
FIG. 1 shows a longitudinal length of an endotracheal tube comprising an irrigation device according to the present invention.

Referring to the figures and, in particular, to FIG. 1, the numeral "1" indicates, in general, an endotracheal tube of plastic material for artificial ventilation of known type (except for details specifically illustrated which constitute the invention). The endotracheal tube 1 comprises a main tubular structure 2 provided at one end (proximal end) with a coupling 3 for connection to an automatic respiration system of known type (not shown), and at the other end (distal end) with a balloon 4, also of known type, adapted to be inflated by air in order to adhere to the trachea of the patient and to be used for known functions.

The air for the inflation of the balloon 4 is fed to the latter through a secondary flexible canalization or inflation cannula 5 of plastic material which extends along and is developed on the inside of the main tubular structure 2, adhering to the inner wall of the latter, or preferably within the thickness of the wall itself. The cannula 5, emerges near the proximal end of the main tubular structure 2 itself, and is associated with a coupling 6 for connection to a flow-generating system.

Towards the proximal end of the main tubular structure 2 there also commences another secondary flexible canalization or irrigation cannula, indicated generally as 7. Cannula 7 is also formed of plastic material and is of constant cross-section in its three sections of development described below. Cannula 7 is also equipped at its proximal end with a coupling 8, provided with pin 9 that is adapted to be associated with a syringe or hypodermic syringe (not shown).

Figure 2:
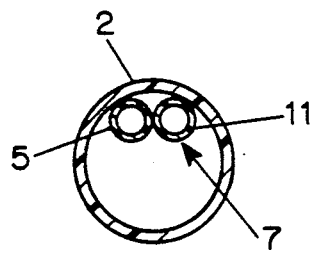
FIGS. 2 and 3 show two cross sections, respectively, through the endotracheal tube of FIG. 1 taken at lines A-A1 and B-B1 in FIG. 1, respectively.

The irrigation cannula 7, which constitutes an aspect of the present invention, is developed over its first portion or proximal portion 10 on the outside of the main tubular structure 2 without adhering to it. The irrigation cannula 7 is inserted into the main tubular structure 2 and has a second or central portion 11 extending within the main tubular structure 2 and adhering to the inner wall of the latter or being within the thickness of the wall itself; alternatively, it may extend within structure 2 in the same way as the inflation cannula 5; see also FIG. 2, which is a cross-section taken at said line A-A1 in FIG. 1.

Figure 3:
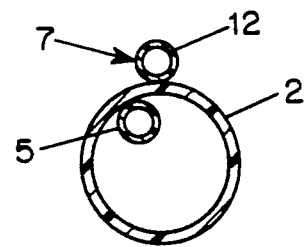

Finally, the irrigation cannula 7 emerges from main tubular structure 2 and extends, over a third or distal portion 12, along the outside of the main tubular structure 2 while it adheres to the outer wall of the distal section of the latter, and even beyond the balloon 4, and terminates with a rounded closed-end 13; see also FIG. 3 which is a cross-section of the unit in this distal section along the line B-B1 of FIG. 1.

The third or distal portion 12 of the irrigation cannula 7, which portion constitutes a true spray device, is provided over its entire length and surface with a plurality of micrometric or small holes 14 for placing its interior side in communication with the outside.

Figure 4:
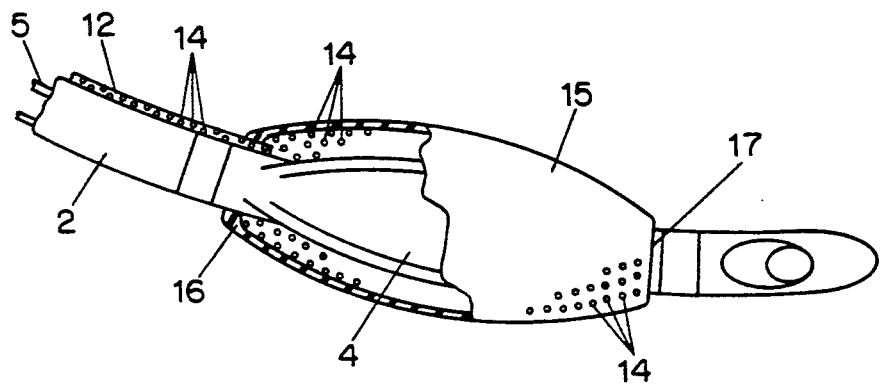
FIGS. 4, 5 and 6 show the distal portion of an endotracheal tube associated with three respective, alternative embodiments of the irrigation device of the invention.

In the variant embodiment shown in FIG. 4, in which only the distal section of the endotracheal tube is shown, the perforated distal portion 12 of the spray cannula 7 debouches into a chamber described and limited by a casing 15. The casing surrounds on the outside, and wraps around so as to enclose, the balloon 4 of the endotracheal tube 1; it is fastened to the latter by upper 16 and lower 17 cuff portions thereof. The outer casing 15 is also provided over its entire surface with micrometric or small holes 14 for placing its interior in communication with the outside. The casing 15 preferably constitutes silicone with high stretchability, even by a low pressure force.

Figure 5:
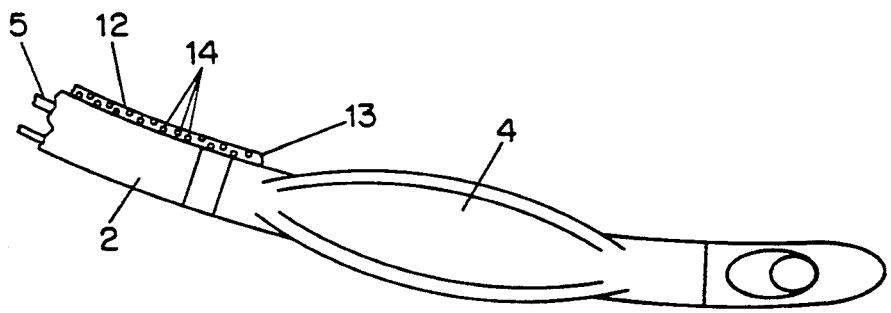

In the variant embodiment shown in FIG. 5, in which there is also shown only the distal section of the endotracheal tube 1, the perforated distal portion 12 of the irrigation cannula 7 stops and terminates with its rounded portion 13 upstream of the balloon 4 of the endotracheal tube 1.

Figure 6:
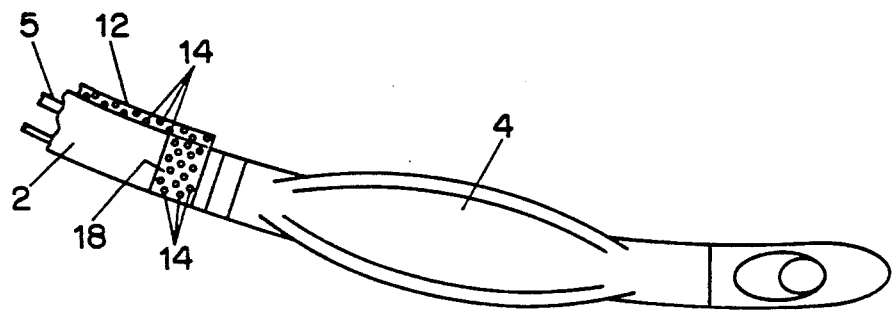

In the variant embodiment shown in FIG. 6, in which there is also shown only the distal section of the endotracheal tube 1, the perforated distal portion 12 of the irrigation cannula 7 debouches into a ring-shaped chamber provided within a cylindrical cuff 18 with double walls welded together at the bases; cuff 18 surrounds the endotracheal tube 1. The cylindrical cuff 18 is also provided over all of its own outer surface with micrometric or small holes 14 adapted to place the ring-shaped chamber described by it in communication with the outside; cuff 18 is formed preferably of silicone, and is preferably arranged in non-protruding fashion on the outer surface of the endotracheal tube 1, fixed around tube 1 by a suitable groove provided on the endotracheal tube 1 itself.

Figure 7:
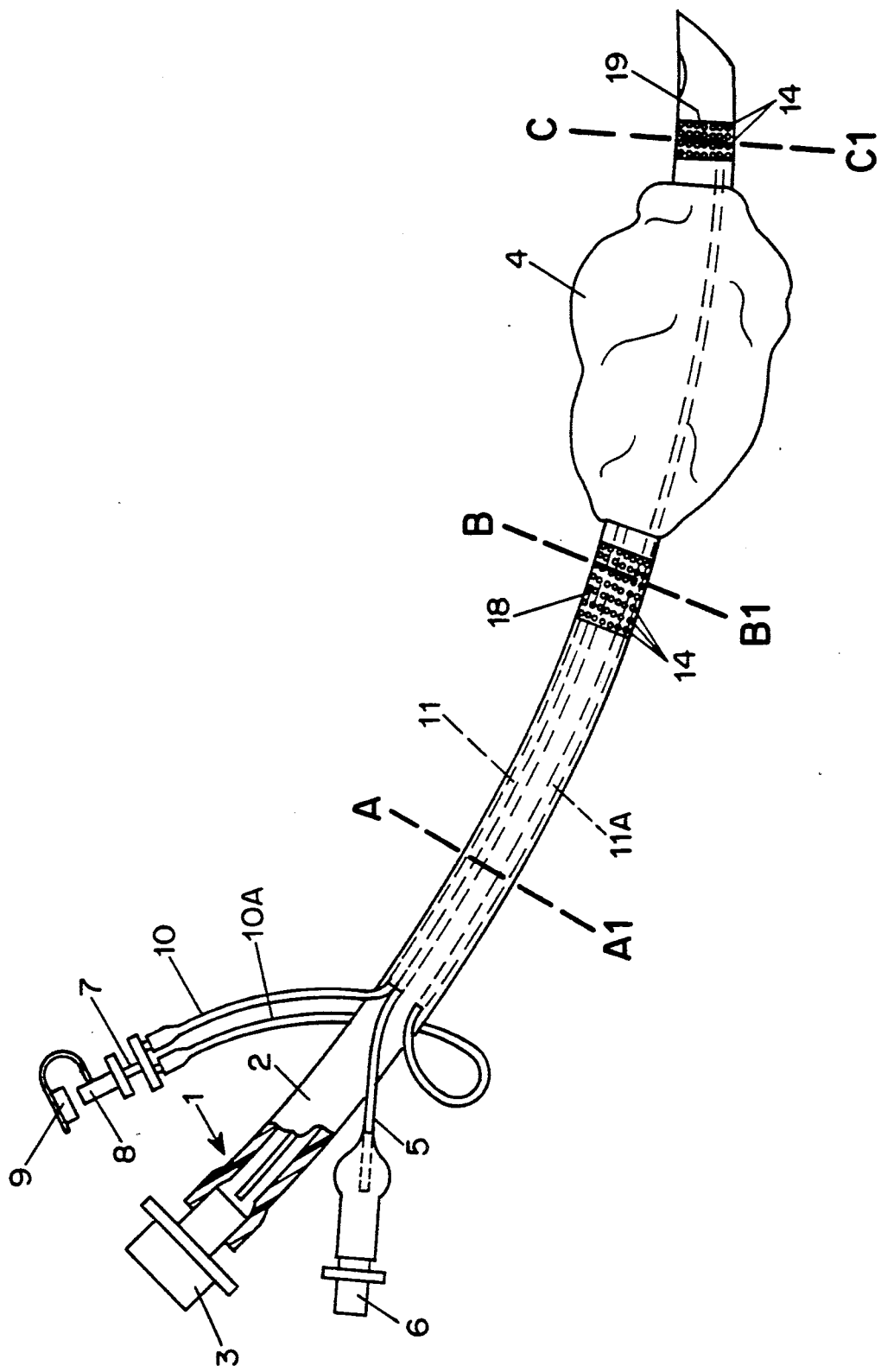
FIG. 7 shows a longitudinal length of an endotracheal tube comprising another alternative embodiment of the irrigation device of the invention.
Figure 8:
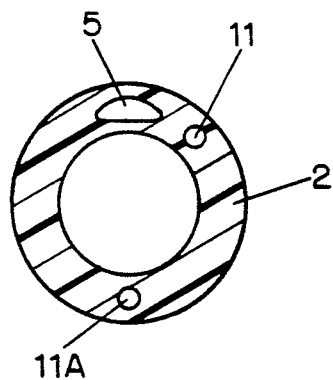
FIGS. 8, 9 and 10 show respective cross-sections through the endotracheal tube of FIG. 7 taken at lines A-A1, B-B1 and C-C1 in FIG. 7, respectively.

FIG. 7 shows another alternative embodiment of the endotracheal tube according to the present invention, in which the irrigation cannula 12 (FIG. 1) is split into two proximal portions 10 and 10A outside the main tubular structure 2; such portions 10 and 10A are engaged within the structure 2 and extend in two portions 11 and 11A within the thickness of the wall of said main tubular structure 2, like the inflation cannula 5 of the balloon 4; see also FIG. 8 which is a cross section through the entire unit in said section along the line A-A1 of FIG. 7.

Figure 9:
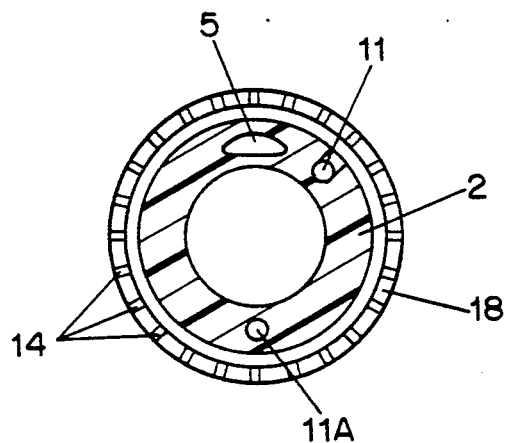

The first inner branch 11 of the irrigation cannula 7 debouches into a ring-shaped chamber contained within a first cylindrical cuff 18 located proximally with respect to the balloon 4; such cuff 18 has the same characteristics as that described above and bearing the same number in FIG. 6; and, for instance, is also provided with a plurality of micrometric or small holes 14 on its own outer surface; see also FIG. 9 which is a cross-section through the entire unit in this section along the line B-B1 of FIG. 7.

Figure 10:
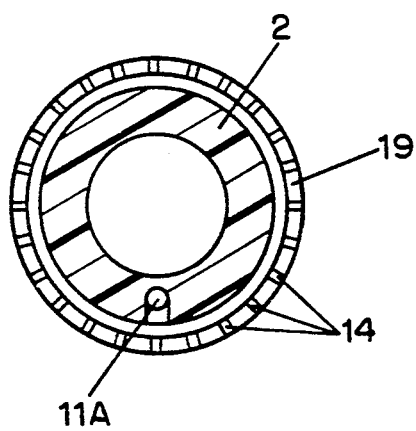

The second inner branch 11A of the irrigation cannula 7, however, continues beyond the balloon 4, below it, and debouches into a further ring-shaped chamber provided within a second cuff 19 located distally with respect to the balloon 4. The cuff 19 has the same characteristics as the cuff 18 referred to above and is also provided with a plurality of micrometric or small holes 14 on its outer surface; see also FIG. 10 which is a cross section of the entire unit in said section, along the line C-C1 of FIG. 7.

In operation, an endotracheal tube 1 is used in known manner to intubate a patient; after the intubation has been effected and at some time during the surgical operation or the intensive resuscitation treatment, the patient can be administered or re-administered a dose of a drug, broadly defined to include local anesthetic, anti-inflammatory or fluidizer intended to carry out its action locally on the laryngotracheal mucosa; this may occur possibly after inflation of the endotracheal balloon 4 in order to permit contact of the drug also with the underlying tracheal mucosae. This administration is effected by injecting, with a syringe a hypodermic syringe, a suitable dose of drug into the irrigation cannula 7 through the coupling 8.

The drug which is thus injected reaches, through the proximal portion 10 and medial portion 11 of the irrigation cannula 7, the distal portion 12 thereof and, from the latter, emerges sprayed through the holes 14, so as to expand on the laryngotracheal mucosae, irrigating them and carrying out its intrinsic action.

In the variant embodiment shown in FIG. 4, the drug enters into the external casing 15 and emerges from the holes 14 provided on the surface thereof, resulting in a more uniform distribution over the entire tracheal mucosae. The perforated outer casing 15 does not prevent the functional expansion of the underlying balloon 4 of the endotracheal tube 1 owing to the substantial elasticity which characterizes it; nor does casing 15 constitute an impediment to intubation as it does not extend substantially beyond the profile of the endotracheal tube 1, like the underlying balloon 4, when deflated.

In the variant embodiment shown in FIG. 5, the perforated distal portion 12 of the irrigation cannula 7 is shorter in order not to interfere with the expansion of the balloon 4 of the endotracheal tube 1.

In the embodiment shown in FIG. 6, the drug reaches into the ring-shaped chamber formed by the cuff 18 and emerges as spray through the holes 14 to achieve a more homogeneous diffusion over the entire endotracheal mucosa.

In the embodiment shown in FIG. 7, the drug is distributed in the two branches 11 and 11A of the irrigation cannula 7, and from the latter enters into the ring-shaped chambers respectively formed by the upper cuff 18 and lower cuff 19. The drug emerges as spray from the holes 14 to achieve an even more diffuse irrigation of the mucosa.

It is obvious that the shaping and location of the irrigation chambers, when provided, can differ from those illustrated above, subject to the concept of the solution described above and claimed below; thus, subject to the same concept of solution, the conformation of the spray holes can also be different; for instance with a spiraling course on the distal portion of the spray cannula, which latter can furthermore be provided with internal spirals or the like in order to impart turbulence to the flow the drug.

It is obvious, finally, that subject to the preferred use of the invention in the field of endotracheal tubes, the spray device of the present invention can find useful and functional application also in medical-surgical tubes and catheters having different functions.

As is evident from the above description of preferred, but not exclusive, embodiments, the spray device of the present invention advantageously provides a means permitting the administration of, possibly repeated administration of, and a homogenous diffusion of, drugs of the type including local anesthetics, anti-inflammatories and mucolytics with constant intubation with endotracheal tube. Such provision of drugs occurs without substantially complicating the intubation or making it more traumatic for the patient; for instance, the overall structure of the instrument is not made in any way rigid, nor is the corresponding cross section changed; furthermore, the drug administrative is achieved without interfering with the functions of the endotracheal tube with which it is associated.

Moreover, the possibility afforded by the invention of repeating the topical anesthesia with constant intubation results, in the course of general anesthesias, in an appreciable savings of neuroleptics, analgesics, halogenated gaseous anesthetics and, in particular muscle relaxants; as well as in permitting the subjecting to general anesthesia of patients who are otherwise inoperable or subject, at times, to lethal post-operative complications.

In addition, there are eliminated or substantially reduced complications of protracted intubations such as dysphonia, laryngitis and formation of mucus plugs, thereby improving the tolerance to respiratory prosthesis as well as the quality of the post-operative wakening and of the period following the extubation.

Furthermore, in the treatments of patients subjected to intensive resuscitation therapy, the adaptation of such patients to the endotracheal tube and, through it, to an automatic respirator is frequently permitted by repeated administrations of tranquilizing drugs, analgesics, muscle relaxants and halogenated gaseous anesthetics. With the spray device according to the present invention in such operations, in addition to considerably reducing the dosage of such drugs, local complications such as cardiovascular complications are reduced and, in particular, there can be reduced the recourse to a tracheostomy as a consequence of repeated traumatisms of the balloon of the endotracheal tube on the mucosae.

It should be understood that the preferred embodiments and examples described are for illustrative purposes only and are not to be construed as limiting the scope of the present invention which is properly delineated only in the appended claims.

I claim:

1. An endotracheal tube with provision for delivering a drug externally of the tube, comprising:
   an endotracheal tube body having proximal and distal ends and a balloon portion at said distal end;
   at least one flexible irrigation cannula extending along said endotracheal tube body to said distal end divided in its proximal portion into two branch cannulas;
   an irrigation diffuser means comprising a pair of chambers respectively circumscribed by a pair of cuffs located proximally and distally with respect to said balloon portion, respectively, said cuffs each comprising a double wall, and outer wall of each cuff having a plurality of small holes for emitting a drug; and
   a pair of grooves opening outwardly of said tube body for respectively containing said pair of cuffs without substantial protrusion of said cuffs beyond a main outer surface of said body.

2. An endotracheal tube according to claim 1 wherein said irrigation cannula is provided at its proximal end with a coupling adapted to connect it to a syringe.

* * * * *